United States Patent
Lee

(10) Patent No.: US 7,905,379 B2
(45) Date of Patent: Mar. 15, 2011

(54) HAMMER-DRIVE POWDER-ACTUATED TOOL

(76) Inventor: Chung-Yi Lee, Taipei (TW)

(*) Notice: Subject to any disclaimer, the term of this patent is extended or adjusted under 35 U.S.C. 154(b) by 16 days.

(21) Appl. No.: 12/582,577

(22) Filed: Oct. 20, 2009

(65) Prior Publication Data

US 2010/0252609 A1    Oct. 7, 2010

(30) Foreign Application Priority Data

Apr. 1, 2009  (TW) ............................... 98205212 U

(51) Int. Cl.
 *B25C 1/14* (2006.01)
(52) U.S. Cl. .......................................................... 227/10
(58) Field of Classification Search ................ 227/9, 10, 227/130; 123/46 SC
See application file for complete search history.

(56) References Cited

U.S. PATENT DOCUMENTS

| | | | | |
|---|---|---|---|---|
| 4,598,851 A * | 7/1986 | Kopf | | 227/9 |
| 4,821,938 A * | 4/1989 | Haytayan | | 227/10 |
| 4,867,365 A * | 9/1989 | Buechel et al. | | 227/10 |
| 4,945,730 A * | 8/1990 | Laney | | 60/635 |
| 5,170,922 A * | 12/1992 | Ehmig et al. | | 227/8 |
| 5,310,108 A * | 5/1994 | Popovich et al. | | 227/10 |
| 5,429,291 A * | 7/1995 | Thompson | | 227/10 |
| 5,992,723 A * | 11/1999 | Lee | | 227/9 |
| 6,126,055 A * | 10/2000 | Gantner et al. | | 227/10 |
| 6,364,190 B1 * | 4/2002 | Tor | | 227/10 |
| 7,048,166 B2 * | 5/2006 | Pfister et al. | | 227/9 |

* cited by examiner

*Primary Examiner* — Scott A. Smith
(74) *Attorney, Agent, or Firm* — Pepper Hamilton LLP

(57) ABSTRACT

A hammer-drive powder-actuated tool includes: a barrel unit inserted movably into a tubular housing; a firing pin holder disposed fixedly in the housing, abutting against a rear end portion of the barrel unit and formed with a through hole; a firing pin disposed movably between a rear open end of the housing and the rear end portion of the barrel unit, having an intermediate portion interconnecting integrally a firing end portion that extends into the through hole in the firing pin holder and a head portion, and operable between a normal position and a firing position; an engaging member sleeved on the intermediate portion of the firing pin for stopping movement of the firing end portion of the firing pin away from the through hole in the firing pin holder; and a biasing member for biasing the firing pin to move toward the normal position.

9 Claims, 5 Drawing Sheets

HAMMER-DRIVE POWDER-ACTUATED TOOL

CROSS-REFERENCE TO RELATED APPLICATION

This application claims priority of Taiwanese Application No. 098205212, filed on Apr. 1, 2009.

BACKGROUND OF THE INVENTION

1. Field of the Invention

The invention relates to a fastener driver, more particularly to a hammer-drive powder-actuated tool.

2. Description of the Related Art

Referring to FIG. 1, a conventional hammer-drive powder-actuated tool 1 is shown to include a tubular housing 11 having a front open end 111 and an enlarged rear open end 112, a barrel unit 12 inserted movably into the housing 11 via the front open end 111 of the housing 11, a piston assembly 14 disposed movably in the barrel unit 12, a sleeve 13 coupled to a rear end of the barrel unit 12 and defining a chamber 131 for receiving powder load therein, a firing pin holder 15 disposed in the housing 11, abutting against the sleeve 13 and having a through hole 151, a firing pin 16 mounted movably in the through hole 151 and operable between a normal position and a firing position, and a compressed spring 17 sleeved on the firing pin 16 for biasing the firing pin 16 to move toward the normal position and for providing a desired preset biasing force (normally more than 60 lbs.) on the firing pin 16 at the normal position.

The firing pin 16 includes a pin body 161 and a nut 162. The pin body 161 is in the form of a bolt. The pin body 161 has an enlarged firing end portion 1611 disposed adjacent to the sleeve 13, spaced apart from the powder load in the chamber 131 in the sleeve 13 when the firing pin 16 is at the normal position, as shown in FIG. 1, and contacting and igniting the powder load in the chamber 131 in the sleeve 13 when the firing pin 16 is at the firing position, and a threaded end portion 1612 opposite to the firing end portion 1611 and disposed adjacent to the rear open end 112 of the housing 11. The nut 162 is connected threadedly to the threaded end portion 1612 of the pin body 161. A positioning pin 163 extends radially through the nut 162 and the threaded end portion 1612 of the pin body 161 so as to prevent movement of the nut 162 relative to the threaded end portion 1612 of the pin body 161. The compressed spring 17 has opposite ends abutting respectively against the nut 162 and an inwardly extending shoulder portion 152 of an inner annular surface defining the through hole 151. In use, the firing pin 16 is moved from the normal position to the firing position through beating by a hammer with a sufficient force which can overcome the preset biasing force of the spring 17 on the threaded end portion 1612 of the pin body 161.

It is noted that, in order to prevent rotation of the pin body 161 with the nut 162 when screwing the nut 162 onto the pin body 161 during assembly, the firing end portion 1611 of the pin body 161 is shaped as a polygon, such as a hexagon, such that the through hole 151 has a polygonal hole portion 1511, such as a hexagonal hole section, corresponding to the firing end portion 1611. As a result, the firing pin holder 15 cannot be formed by lathe due to a relatively complicated configuration thereof. Furthermore, the firing pin holder 15 is riveted to the housing 11, meanwhile, each of the nut 162 and the threaded end portion 1612 of the pin body 161 must be formed with a through hole (not shown) for permitting extension of the positioning pin 163 there through. Therefore, the conventional powder-actuated tool 1 is fabricated at a relatively high cost. Moreover, since the compressed spring 17 is positioned in the housing 11 through engagement between the nut 162 and the threaded end portion 1612 of the pin body 161, and insertion of the positioning pin 163 into the nut 162 and the threaded end portion 1612 of the pin body 161, it takes a relatively long period of time during assembly.

SUMMARY OF THE INVENTION

Therefore, an object of the present invention is to provide a hammer-drive powder-actuated tool that can overcome the aforesaid drawbacks of the prior art.

According to the present invention, a hammer-drive powder-actuated tool comprises:

a tubular housing having front and rear open ends opposite to each other in an axis, an inner annular surface, and an inner engaging flange extending inwardly and radially from said inner annular surface and disposed adjacent to the rear open end;

a barrel unit inserted movably into the housing through the front open end and having a rear end portion that defines a chamber adapted for accommodating powder load therein; and a firing unit including
 a firing pin holder disposed fixedly in the housing, and formed with a through hole,
 a firing pin disposed movably between the rear open end of the housing and the rear end portion of the barrel unit, the firing pin having a firing end portion that extends into the through hole in the firing pin holder, an enlarged head portion opposite to the firing end portion in the axis and disposed adjacent to the rear open end of the housing, an intermediate portion interconnecting integrally the head portion and the firing end portion, and an annular shoulder portion disposed at a junction of the firing end portion and the intermediate portion, the firing pin being operable between a normal position, where the firing end portion is spaced apart from the powder load in the chamber in the rear end portion of the barrel unit, and a firing position, where the firing end portion contacts and ignites the powder load in the chamber in the rear end portion of the barrel unit,
 an engaging member sleeved on the intermediate portion of the firing pin, and engaged between and abutting against the inner engaging flange of the housing and the firing pin holder so as to prevent movement of the firing end portion of the firing pin away from the through hole in the firing pin holder, and
 a biasing member disposed in the housing and having opposite ends abutting respectively against said head portion of said firing pin and said engaging member for biasing the firing pin to move toward the normal position, thereby enabling the annular shoulder portion of the firing pin to abut against the engaging member.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
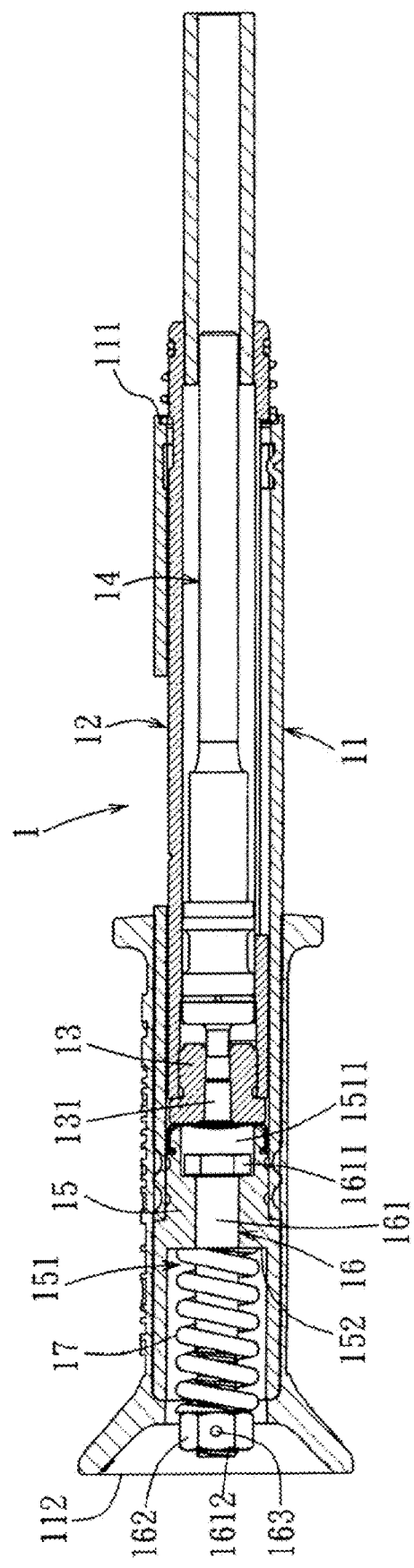
FIG. 1 is a schematic sectional view showing a conventional hammer-drive powder-actuated tool when a firing pin is at a normal position.
Figure 2:
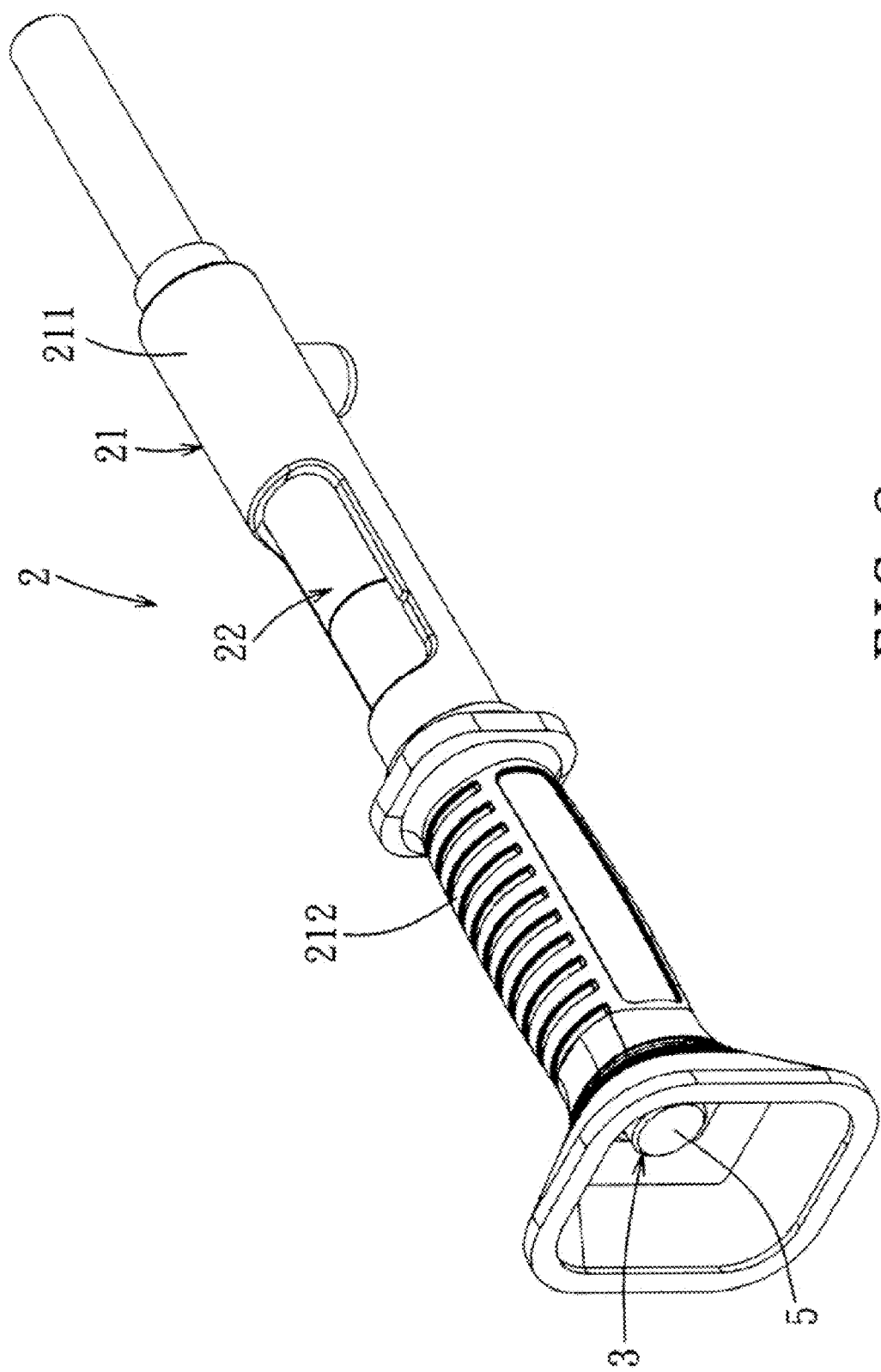
FIG. 2 is a perspective view showing the preferred embodiment of a hammer-drive powder-actuated tool according to the present invention.
Figure 3:
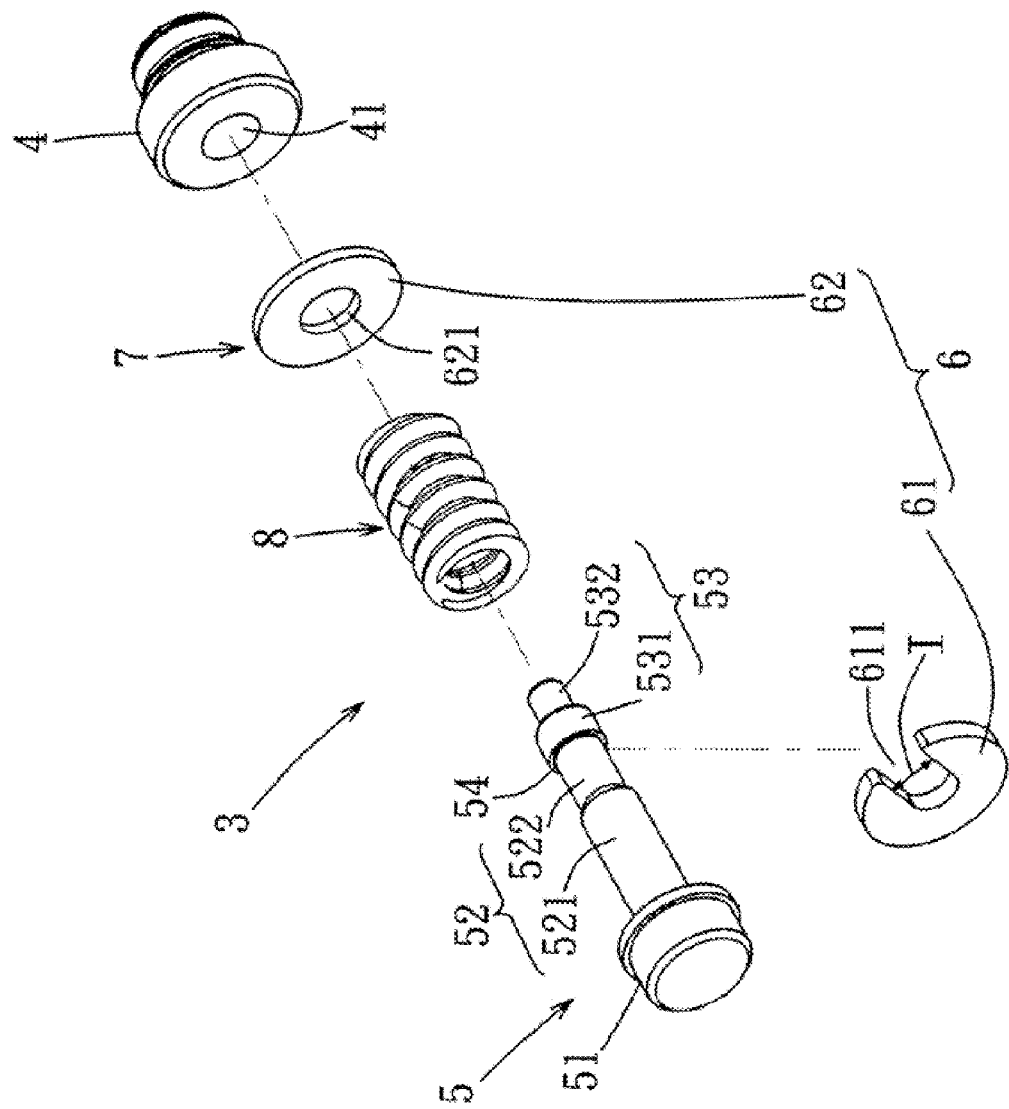
FIG. 3 is an exploded perspective view showing a firing unit of the preferred embodiment.
Figure 4:
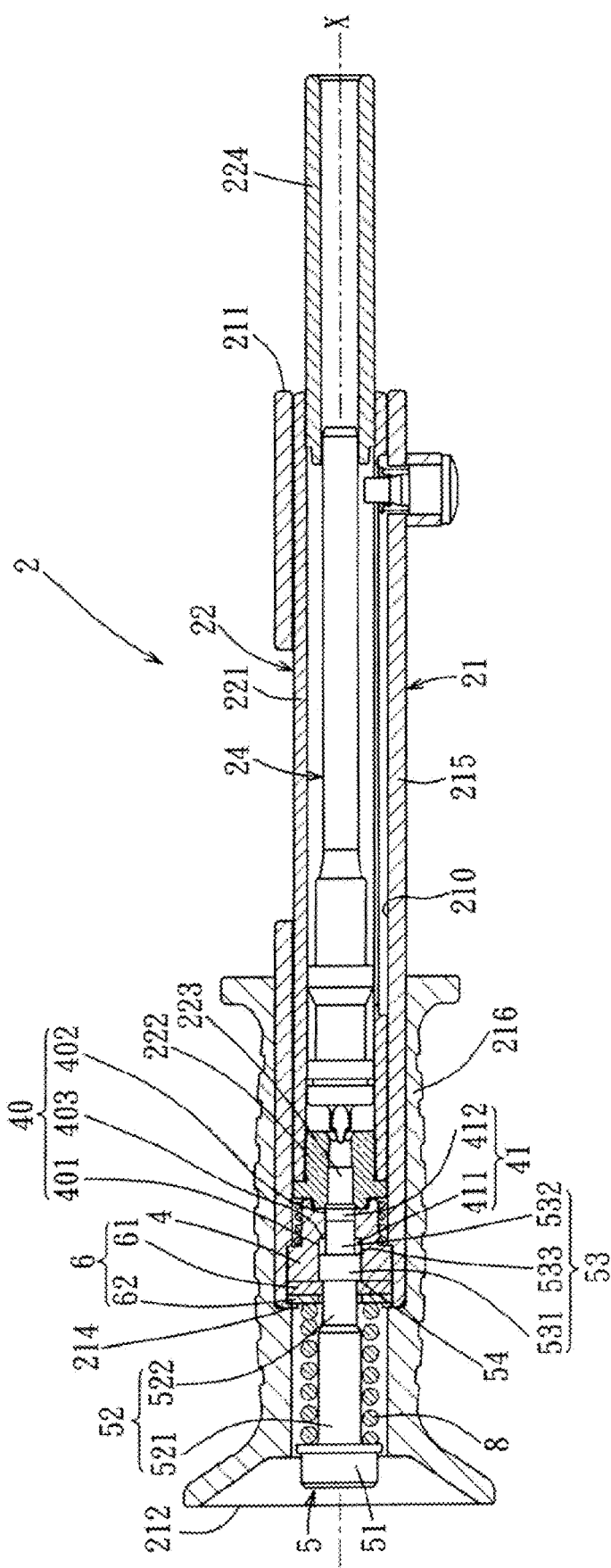
FIG. 4 is a schematic sectional view showing the preferred embodiment when a firing pin of the firing unit is at a normal position.

Referring to FIGS. 2 to 4, the preferred embodiment of a hammer-drive powder-actuated tool 2 according to the present invention is shown to include a tubular housing 21, a barrel unit 22, a piston assembly 24, and a firing unit 3.

The housing 21 has a front open end 211 and a rear open end 212 opposite to each other in an axis (X), an inner annular surface 210, and an inner annular engaging flange 214 extending inwardly and radially from the inner annular surface 210 and disposed adjacent to the rear open end 212. In this embodiment, the housing 21 includes a main tube 215 and a handle sleeve 216. The main tube 215 has a first end serving as the front open end 211, and a second end opposite to the first end in the axis (X). The main tube 215 is formed with an annular flange extending inwardly and radially from the second end and serving as the inner annular engaging flange 214 of the housing 21. The handle sleeve 216 is sleeved fixedly and partially on the main tube 215, and has an enlarged end that serves as the rear open end 212 of the housing 21.

The barrel unit 22 is inserted movably into the housing 21 through the front open end 211 for receiving the piston assembly 24 therein. In this embodiment, the barrel unit 22 includes a thinner first barrel 224, a thicker second barrel 221 connected threadedly to a rear end of the first barrel 224, and a sleeve 222 serving as a rear end portion of the barrel unit 22, and inserted into and connected threadedly to a rear end of the second barrel 221. The sleeve 222 defines a chamber 223 adapted for accommodating powder load (not shown) therein. The firing unit 3 includes a firing pin holder 4, a unitary firing pin 5, an engaging member 6 and a biasing member 8.

The firing pin holder 4 is disposed fixedly in the housing 21, abuts against the rear end portion of the barrel unit 22, i.e., the sleeve 222, and is formed with a through hole 41. In this embodiment, the through hole 41 has a first hole portion 411, and a second hole portion 412 disposed adjacent to the sleeve 222 of the barrel unit 22 and having a diameter smaller than that of the first hole portion 411. The through hole 41 is defined by an inner annular surface 40 that has a first surface portion 401 defining the first hole portion 411, a second surface portion 402 defining the second hole portion 412, and a shoulder portion 403 interconnecting the first and second surface portion 401, 402, as shown in FIG. 4.

Figure 5:
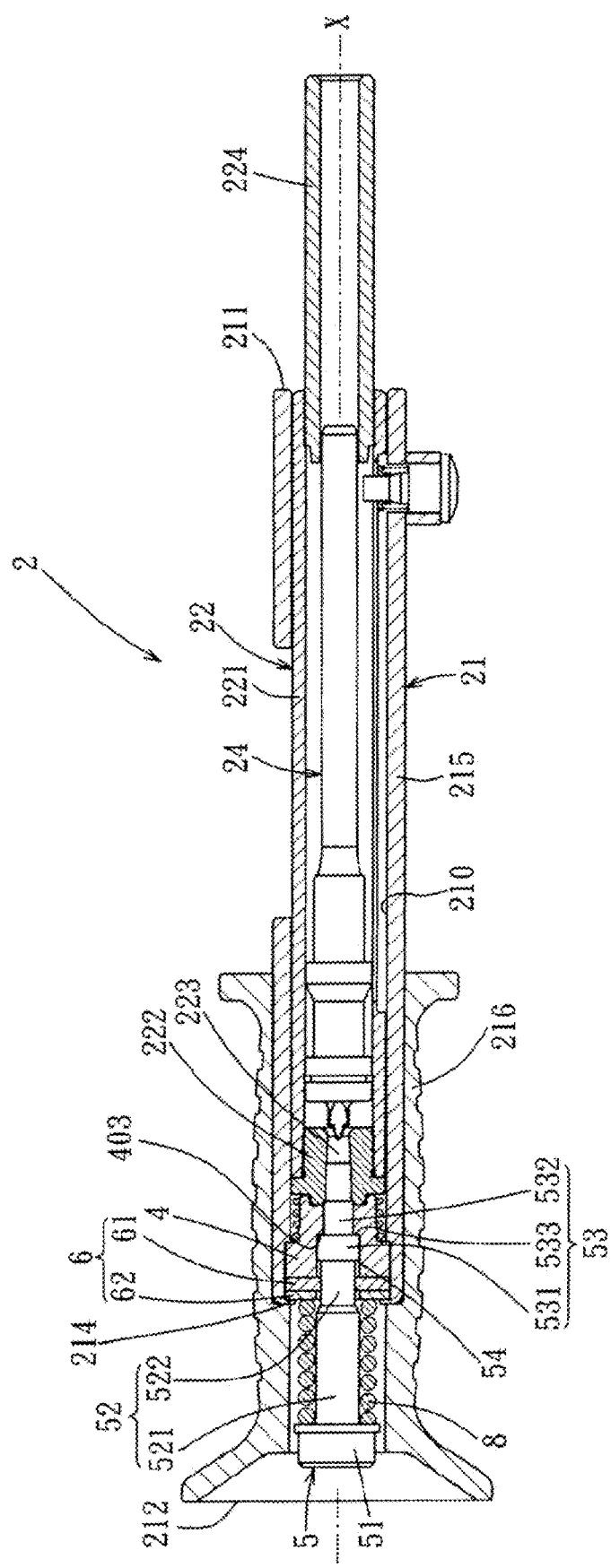
FIG. 5 is a schematic sectional view showing the preferred embodiment when the firing pin of the firing unit is at a firing position.

The firing pin 5 is disposed movably between the rear open end 212 of the housing 21 and the sleeve 222 of the barrel unit 22. The firing pin 5 has a firing end portion 53 that extends into the through hole 41 in the firing pin holder 4, an enlarged head portion 51 opposite to the firing end portion 53 in the axis (X) and disposed adjacent to the rear open end 212 of the housing 21, an intermediate portion 52 interconnecting integrally the head portion 51 and the firing end portion 53, and an annular shoulder portion 54 disposed at a junction of the firing end portion 53 and the intermediate portion 52. The firing pin 5 is operable between a normal position, where the firing end portion 53 is spaced apart from the powder load in the chamber 223 in the sleeve 222 of the barrel unit 22, as shown in FIG. 4, and a firing position, where the firing end portion 53 contacts and ignites the powder load in the chamber 223 in the sleeve 222 of the barrel unit 22. In this embodiment, the firing end portion 53 has a large-diameter section 531 connected integrally to the intermediate portion 52 and movable in the first hole portion 411 of the through hole 41 in the firing pin holder 4, a small-diameter section 532 opposite to the large-diameter section 531 in the axis (X), extending into the second hole portion 412 of the through hole 41 in the firing pin holder 4, and adapted to contact the powder load when the firing pin 5 is at the firing position (see FIG. 5), and a shoulder portion 533 interconnecting integrally the large-diameter section 531 and the small-diameter section 532, and abutting against the shoulder portion 403 of the inner annular surface 40 of the firing pin holder 4 when the firing pin 5 is at the firing position (see FIG. 5). The intermediate portion 52 has a first section 521 connected integrally to the head portion 51, and a second section 522 interconnecting integrally the first section 521 and the large-diameter section 531 of the firing end portion 53. The second section 522 of the intermediate portion 52 has a diameter smaller than those of the first section 521 of the intermediate portion 52 and the large-diameter section 531 of the firing end portion 53 such that the annular shoulder portion 54 is defined between the second section 522 of the intermediate portion 52 and the large-diameter section 531 of the firing end portion 53.

The engaging member 6 is sleeved on the intermediate portion 52 of the firing pin 5, and is engaged between and abuts against the inner annular engaging flange 214 of the housing 21 and the firing pin holder 4 so as to stop movement of the firing end portion 53 of the firing pin 5 away from the through hole 41 in the firing pin holder 4. In this embodiment, the engaging member 6 includes a C-shaped ring 61 and a washer 62. The C-shaped ring 61 is engaged on the second section 522 of the intermediate portion 52 of the firing pin 5, abuts against the firing pin holder 4, and has an opening 611 that has a width (l) substantially equal to a diameter of the second section 522 of the intermediate portion 52 of the firing pin 5, as shown in FIG. 3. The C-shaped ring 61 abuts against the annular shoulder portion 54 of the firing pin 5 when the firing pin 5 is at the normal position, as shown in FIG. 4, thereby preventing movement of the firing end portion 53 of the firing pin 5 away from the through hole 41 in the firing pin holder 4. The washer 52 is sleeved on the second section 522 of the intermediate portion 52 of the firing pin 5, and has a center through hole 621 that has a diameter larger than that of the large-diameter section 531 of the firing end portion 53 of said firing pin 5.

In this embodiment, the biasing member 8 is a compressed spring disposed in the housing 21, sleeved on the intermediate portion 52 of the firing pin 5, and having opposite ends abutting respectively against the head portion 51 of the firing pin 5 and the washer 62 of the engaging member 6 for biasing the firing pin 5 to move toward the normal position, thereby enabling the annular shoulder portion 54 of the firing pin 5 to abut against the C-shaped ring 61 of the engaging member 6.

During assembly, an assembly of the firing pin 5, the engaging member 6 and the biasing member 8 is formed first, wherein the biasing member 8 and the washer 62 are sleeved on the firing pin 5 in order, and then the washer 62 is pushed by a tool (not shown) to move away from the annular shoulder portion 54 such that the C-shaped ring 61 can be sleeved on the second section 522 of the intermediate portion 52 via the opening 611 last. As a result, the biasing member 8 is precompressed so as to generate a biasing force for biasing the annular shoulder portion 54 to abut against the engaging member 6 when the firing pin 5 is at the normal position and for providing a desired preset force to minimize inadvertent firing of the powder load. The preset force must be overcome before the firing pin 5 contacts and ignites the powder load. Subsequently, the firing pin holder 4, and the assembly of the firing pin 5, the engaging member 6 and the biasing member 8 are disposed in the housing 21 in order. Finally, the inner annular engaging flange 214 is formed using a tool (not shown).

In such a configuration, the through hole 41 in the firing pin holder 4 is circular and can be formed by lathe. Therefore, the hammer-drive powder-actuated tool 2 of the present invention has a relatively low processing cost. The firing pin 5, the engaging member 6 and the biasing member 8 can be easily assembled together without engagement of the nut 162 and insertion of the positioning pin 163 required in the aforesaid prior art such that it takes a relatively short period of time during assembly. Furthermore, since the firing pin 5 is integrally formed, the head portion 51 has a better appearance as compared to an assembly of the nut 162 and the threaded end portion 1612 and the positioning pin 163 of the aforesaid conventional hammer-drive powder-actuated tool 1.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A hammer-drive powder-actuated tool comprising:
a tubular housing having front and rear open ends opposite to each other in an axis, an inner annular surface, and an inner engaging flange extending inwardly and radially from said inner annular surface and disposed adjacent to said rear open end;
a barrel unit inserted movably into said housing through said front open end and having a rear end portion that defines a chamber adapted for accommodating powder load therein; and
a firing unit including
a firing pin holder disposed fixedly in said housing, and formed with a through hole,
a firing pin disposed movably between said rear open end of said housing and said rear end portion of said barrel unit, said firing pin having a firing end portion that extends into said through hole in said firing pin holder, an enlarged head portion opposite to said firing end portion in the axis and disposed adjacent to said rear open end of said housing, an intermediate portion interconnecting integrally said head portion and said firing end portion, and an annular shoulder portion disposed at a junction of said firing end portion and said intermediate portion, said firing pin being operable between a normal position, where said firing end portion is spaced apart from the powder load in said chamber in said rear end portion of said barrel unit, and a firing position, where said firing end portion contacts and ignites the powder load in said chamber in said rear end portion of said barrel unit,
an engaging member sleeved on said intermediate portion of said firing pin, and engaged between and abutting against said inner engaging flange of said housing and said firing pin holder so as to stop movement of said firing end portion of said firing pin away from said through hole in said firing pin holder, and
a biasing member disposed in said housing and having opposite ends abutting respectively against said head portion of said firing pin and said engaging member for biasing said firing pin to move toward the normal position, thereby enabling said annular shoulder portion of said firing pin to abut against said engaging member.

2. The hammer-drive powder-actuated tool as claimed in claim 1, wherein said engaging member includes a C-shaped ring sleeved and engaged on said intermediate portion of said firing pin and abutting against said firing pin holder.

3. The hammer-drive powder-actuated tool as claimed in claim 2, wherein said engaging member further includes a washer sleeved on said intermediate portion of said firing pin, and disposed between and abutting against said C-shaped ring and said inner engaging flange of said housing.

4. The hammer-drive powder-actuated tool as claimed in claim 3, wherein said washer has a center through hole that has a diameter larger than that of said firing end portion of said firing pin.

5. The hammer-drive powder-actuated tool as claimed in claim 1, wherein:
said firing end portion of said firing pin has a large-diameter section connected integrally to said intermediate portion, a small-diameter section opposite to said large-diameter section in the axis, having a diameter smaller than that of said large-diameter section and adapted to contact the powder load when said firing pin is at the firing position, and a shoulder portion interconnecting integrally said large-diameter section and said small-diameter section; and
said through hole in said firing pin holder has a first hole portion disposed adjacent to said engaging member and permitting movement of said large-diameter section of said firing end portion of said firing pin therein, and a second hole portion disposed adjacent to said rear end portion of said barrel unit, having a diameter smaller than that of said first hole portion and permitting extension of said small-diameter section of said firing end portion of said firing pin thereinto, said through hole in said firing pin holder being defined by an inner annular surface that has a first surface portion defining said first hole portion, a second surface portion defining said second hole portion, and a shoulder portion interconnecting said first and second surface portions, and abutting against said shoulder portion of said firing end portion of said firing pin when said firing pin is at the firing position.

6. The hammer-drive powder-actuated tool as claimed in claim 5, wherein said intermediate portion of said firing pin has a first section connected integrally to said head portion of said firing pin, and a second section interconnecting integrally said first section and said firing end portion of said firing pin, and sleeved with said engaging member thereon, said second section of said intermediate portion of said firing pin having a diameter smaller than those of said first section of said intermediate portion and said first section of said firing end portion such that said annular shoulder portion is defined between said second section of said intermediate portion and said first section of said firing end portion, and abuts against said engaging member due to a biasing force generated by said biasing member when said firing pin is at the normal position, thereby preventing movement of said firing end portion of said firing pin away from said through hole in said firing pin holder.

7. The hammer-drive powder-actuated tool as claimed in claim 1, wherein said housing includes:
- a main tube having a first end that serves as said front open end, and a second end opposite to said first end in the axis, said main tube being formed with an flange extending inwardly and radially from said second end and serving as said inner engaging flange of said housing;
- a handle sleeve sleeved fixedly and partially on said main tube and having an enlarged end that serves as said rear open end of said housing.

8. The hammer-drive powder-actuated tool as claimed in claim 1, wherein said biasing member includes a compressed spring sleeved on said intermediate portion of said firing pin and having said opposite ends.

9. The hammer-drive powder-actuated tool as claimed in claim 1, wherein said intermediate portion of said firing pin interconnects integrally said head portion and said firing end portion of said firing pin.

* * * * *